United States Patent
Drees et al.

(10) Patent No.: US 8,933,421 B2
(45) Date of Patent: Jan. 13, 2015

(54) HALO MONITOR IN ROTATABLE GANTRY FOR PARTICLE BEAM POSITIONING

(75) Inventors: Jürgen Drees, Wuppertal (DE); Helmut Piel, Wuppertal (DE)

(73) Assignee: Varian Medical Systems Particle Therapy GmbH, Bergisch-Gladbach (DE)

(*) Notice: Subject to any disclaimer, the term of this patent is extended or adjusted under 35 U.S.C. 154(b) by 279 days.

(21) Appl. No.: 12/988,763

(22) PCT Filed: Apr. 21, 2009

(86) PCT No.: PCT/EP2009/054747
§ 371 (c)(1),
(2), (4) Date: Jan. 3, 2011

(87) PCT Pub. No.: WO2009/130220
PCT Pub. Date: Oct. 29, 2009

(65) Prior Publication Data
US 2011/0186746 A1    Aug. 4, 2011

(30) Foreign Application Priority Data

Apr. 21, 2008  (DE) .......................... 10 2008 020 039

(51) Int. Cl.
*A61N 5/00* (2006.01)
*A61N 5/10* (2006.01)
*G21K 1/08* (2006.01)

(52) U.S. Cl.
CPC .. *G21K 1/08* (2013.01); *A61N 5/10* (2013.01); *A61N 5/1043* (2013.01); *A61N 5/1048* (2013.01); *A61N 2005/1087* (2013.01)
USPC ..................... 250/492.1; 250/492.22; 250/397

(58) Field of Classification Search
CPC .......... G01T 1/29; G01T 1/20; H05H 13/005; A61N 5/1081
USPC ..................... 250/492.1, 492.22, 492.23, 397
See application file for complete search history.

(56) References Cited

U.S. PATENT DOCUMENTS 4,577,156 A * 3/1986 Kerst ............................ 315/504
4,803,368 A   2/1989 Barthelmes
(Continued)

FOREIGN PATENT DOCUMENTS

DE   60301990 T2   7/2006
EP   1045399 A1   10/2000
(Continued)

OTHER PUBLICATIONS

Cardinal Health "Cylindrical Ion Chambers: Victoreen Model 550 Series" (c) 2003, accessed on May 21, 2012 via http://www.jzimaging.com/IMAGES/Product%20Informaton/Cardinal%20Health/JZ%20Cardinal/RO2jz.pdf.*

(Continued)

*Primary Examiner* — Brooke Purinton
(74) *Attorney, Agent, or Firm* — Alleman Hall McCoy Russell & Tuttle LLP (57) ABSTRACT

A particle beam therapy system including an accelerator for making a beam of charged particles available, a beam guiding unit supplying the beam to a treatment location starting from the accelerator, and at least one beam property monitor arranged along the beam path. A control unit communicates with the beam property monitor and guiding unit and determines deviations of actual properties from desired properties of the beam and transmits control signals for adapting the beam properties to the guiding unit, using said deviations. Precise beam guidance is achieved by arranging the beam property monitor on the periphery of the beam perpendicular to the beam path such that the beam properties are detected due to their direct interaction with particles of the beam in the halo region and/or indirectly by electromagnetic interaction. A method for a beam of charged particles in a particle beam therapy system is also disclosed.

17 Claims, 7 Drawing Sheets

(56) References Cited

U.S. PATENT DOCUMENTS

| | | | | |
|---|---|---|---|---|
| 4,931,653 | A * | 6/1990 | Hamm et al. | 250/385.1 |
| 5,065,420 | A * | 11/1991 | Levene | 378/137 |
| 5,131,021 | A * | 7/1992 | Gard et al. | 378/19 |
| 5,299,250 | A * | 3/1994 | Styrnol et al. | 378/19 |
| 5,335,255 | A * | 8/1994 | Seppi et al. | 378/4 |
| 5,404,018 | A * | 4/1995 | Yasuda et al. | 250/492.22 |
| 6,094,469 | A * | 7/2000 | Dobbs et al. | 378/19 |
| 6,236,050 | B1 * | 5/2001 | Tumer | 250/370.09 |
| 6,459,769 | B1 * | 10/2002 | Cosman | 378/147 |
| 6,683,318 | B1 * | 1/2004 | Haberer et al. | 250/492.3 |
| 6,799,068 | B1 * | 9/2004 | Hartmann et al. | 607/2 |
| 7,479,632 | B1 * | 1/2009 | Gevelber et al. | 250/307 |
| 8,260,013 | B2 * | 9/2012 | Pekar et al. | 382/128 |
| 2002/0121889 | A1 * | 9/2002 | Larsen et al. | 324/71.3 |
| 2005/0094762 | A1 * | 5/2005 | Dunham et al. | 378/19 |
| 2006/0163495 | A1 * | 7/2006 | Hiramoto et al. | 250/492.3 |
| 2007/0086564 | A1 * | 4/2007 | Bruder et al. | 378/9 |
| 2007/0170994 | A1 * | 7/2007 | Peggs et al. | 331/34 |
| 2007/0228291 | A1 * | 10/2007 | Hiramoto et al. | 250/492.3 |
| 2007/0253529 | A1 * | 11/2007 | Seppi | 378/21 |
| 2008/0234531 | A1 * | 9/2008 | Welch et al. | 600/2 |
| 2010/0187425 | A1 * | 7/2010 | Majewski et al. | 250/363.05 |
| 2011/0103551 | A1 * | 5/2011 | Bal et al. | 378/65 |

FOREIGN PATENT DOCUMENTS

| | | |
|---|---|---|
| EP | 1348465 A1 | 10/2003 |
| EP | 1876870 A1 | 1/2008 |
| WO | 0104926 A1 | 1/2001 |
| WO | 2007045076 A1 | 4/2007 |
| WO | 2009106603 A1 | 9/2009 |

OTHER PUBLICATIONS

Peters A et al: "Beam Diagnostics for the Heavy Ion Cancer Therapy Facility" AIp Conference Proceedings, American Institute of Physics, New York, US, No. 546, May 8, 2000, pp. 519-526, XP008003048 ISSN: 0094-243x.

Forck P et al: "A scintillator based halo-detector for beam position monitoring" European Particle Accelerator Conference. Epac, XX, XX, vol. 3, Jun. 14, 1997, pp. 2644-2646, XP009120834 ISBN: 978-0-7503-0386-6.

Eickhoff H et al: "HICAT—the German hospital-based light ion cancer therapy project" Proceedings of the 2003 Particle Accelerator Conference. Pac 2003. Portland, OR, May 12-16, 2003; [Particle Accelerator Conference], New York, NY: IEEE, Us, vol. 1, May 12, 2003, pp. 694-698, XP010700523 ISBN: 978-0-7803-7738-7.

Eickhoff H: "Controls and Beam Diagnostics for Therapy-Accelerators" Proceedings of the Dipac 1999—Chester, UK, 1999, pp. 24-27, XP00256I60I Chester, UK.

Dolling R: "Progress of the Diagnostics at the PROSCAN Beam Lines" Proceedings of the Dipac, 2007, Venice, Italy, 2007, pp. 361-363, XP002561602 Venice, Italy.

Dolling R: "Profile, current, and halo monitors of the PROSCAN beam lines" Eleventh Beam Instrumentation Workshop 2004 May 3-6, 2004 Knoxville, TN, USA, No. 732, 2004, pp. 244-252, XP002561603 AIP Conference Proceedings AIP USA ISSN: 0094-243X; & Database INSPEC [Online] The Institution of Electrical Engineers, Stevenage, GB; 2004, Database accession No. 8350436.

Dolling R: "Ionisation Chambers and Secondary Emission Monitors at the PROSCAN Beam Lines" (Proceedings of the) Beam Instrumentation Workshop 2006: Twelfth Workshop, 2006, pp. 271-280, XP002561604.

Particle Data Group, W.-M. Yao et al., "The Review of Particle Physics" Journal of Physics G33 (2006)1 and update 2008.

Karl L. Brown, Sam K. Howry, "TRANSPORT, A Computer Program for Designing Charged Particle Beam Transport Systems", SLAC Report No. 91 (1970) and later updates of the TRANSPORT program by U. Rohrer and others.

U. Rohrer, "PSI Graphic TURTLE Framework based on a CERN/SLAC/FERMILAB version by K.L. Brown et al.", http://aea.web.psLch/Urs_Rohrer/MyWeb/turtle.htm., Apr. 2, 2011.

J. Drees, "Passage of Protons through Thick Degraders", Cryoelectra Report Sep. 2008.

2006, XP002539474 Retrieved from the internet: URL:http://web.archive.org/web/20061024055 507/http://www.detectors.saint-gobain.com/Data/Element/Node/Category/Category_edit.asp?ele_ch_id=C0000000000000001855&Lang=US> [retrieved on Jul. 30, 2009].

2005, XP002539473 Retrieved from the Internet: URL:http://web.archive.org/web/20060504083 702/www.detectors.saint-gobain.com/Media/Documents/S0000000000000001004/SGC+BC400-40 4-408-412-416+Data+Sheet+0105.pdf> [retrieved on Jul. 30, 2009].

2007, XP002539475 Retrieved from the Internet: URL:http://www.detectors.saint-gobain.com/Media/Documents/S0000000000000001004/SGC_Glass_Scintillator_Data_Sheet.pdf> [retrieved on Jul. 30, 2009].

Peter Strehl Ed—Peter Strehl: "Chapter 2: Beam Intensity Measurements" Beam Instrumentation and Diagnostics (Book Series; Particle Acceleration and Detection), Springer Berlin / Heidelberg, Jan. 1, 2006, pp. 11-70, XP009127184 ISBN: 978-3-540-26401-9 [retrieved on Jun. 18, 2006] Kapeitel 2., 2.4.

* cited by examiner

HALO MONITOR IN ROTATABLE GANTRY FOR PARTICLE BEAM POSITIONING

BACKGROUND OF THE INVENTION

1. Field of the Invention

The invention relates to a particle beam therapy system with an accelerator for generating a beam of charged particles, with a beam guiding unit which guides the beam from the accelerator to a treatment location with at least one beam property monitor arranged along the beam path, and one control unit communicating with the beam property monitor and the beam guiding unit, which determines the deviations of the actual properties from the desired properties of the beam and transmits control signals on the basis of these deviations for adaptation of the beam properties at the beam guiding unit. The invention further relates to a method for guiding a beam of charged particles in a particle beam therapy system.

2. Description of the Related Art

The beam therapy with charged particles, e.g. ions in the form of protons, has considerable advantages over the commonly used beam therapy with photons for patients with certain types of cancers. Irradiation with ions, especially protons, is particularly advantageous since these ions show their maximum ionization strength, and thus their maximum destructive power for tumor cells for instance, only at the end of their path to the tissues to be irradiated, the so-called Bragg peak. The effect on the healthy tissue located off the tissue to be treated and located in the path through which the beam passes can thus be reduced.

A particularly important and complex component of the magneto-optic transport system for guiding the particles from the accelerator to the patient is the carrier frame called the gantry. This carrier frame can be rotated around a rotation axis, preferably horizontal, thus enabling irradiation of the tumor tissue at various angles within a large range of up to about 360° C. The position of the huge beam guiding magnets in the field of gravity changes when the gantry is rotated. This results in a change in the gravitational force as well which can lead to an unforeseeable position deviation of the beam guiding magnets from the desired position (i.e. nominal position). As a result, there are considerable spatial deviations in the centre of the particle beam from the desired position which can lead to momentum deviations along the beam path.

Successful treatment of tumors with a particle beam, e.g. using the raster scan therapy method, necessitates accurate knowledge of beam properties, especially the beam position and the beam momentum, at the treatment location, i.e. the isocenter. Even relatively minor position deviations of multi-pole magnets of the beam guiding system can lead to undesired position deviations of the particle beam at the isocenter. These spatial deviations of the particle beam can be much larger than the position deviations of the multi-pole magnets.

For instance, a rotation-dependent shift of one millimeter of a quadrupole magnet of the gantry which is used as a focusing element can for instance lead to a spatial deviation of up to ten millimeters for the beam at the isocenter. It is difficult to completely prevent deviations (outside the required tolerance) of the beam guiding magnets when rotating the gantry using rigid mounting methods. A correction is thus required to prevent inaccuracies in the treatment.

As known from the patent specification EP 1 348 465 B1, beam deviations should be compensated using correction magnets in the beam guiding system. However, the disadvantage of the known systems is that monitors are used for recording the actual position (i.e. current position) of the beam, which influence the particle beam such that the transmission efficiency of the beam from the accelerator to the treatment location is reduced to a value that is unfavorable for the treatment. The actual position of the beam must thus be adapted to the desired position before the actual treatment. In particle beam therapy systems that are operated using the raster scan therapy method, this can lead to a significant amount of adjustment time.

In addition to the rotation-dependent influences, it can also lead to unforeseeable changes in the beam position if, during the raster scan therapy method, the beam energy is changed in the course of the treatment for instance in order to change the energy input into the tissue to be treated and thus, the penetration depth of the beam. Unforeseeable changes in the beam position can for instance be caused due to hysteresis phenomenon when changing the energizing current in the magnetic field coils of the electromagnets of the beam guiding unit. Current fluctuations in the power supplies of the magnets can also result in unforeseeable variations in the field of the beam guiding magnets.

BREIF SUMMARY OF THE INVENTION

Based on this assumption, the object of this invention is to provide a particle beam therapy system which can ensure accurate beam guiding even during the treatment, especially during the particle beam therapy treatment. In addition, the object of the invention is also to provide a suitable method for guiding a beam of charged particles in a particle beam therapy system.

SUMMARY OF THE INVENTION

According to one of the first theories of this invention, the object is achieved with a particle beam therapy system in accordance with the preamble of the patent claim 1 such that the beam property monitor is arranged on the beam periphery perpendicular to the beam path in such a manner that the beam properties are recorded by means of a direct interaction with the particle of the beam in the halo region.

The idea of enabling automatic guiding of the particle beam by compensating the described deviations of the beam position even during the treatment forms the basis of this invention.

As a result, deviations particularly occurring when, during the treatment, rotating the gantry is necessary, and/or when current fluctuations at the power supplies occur and/or when, during the treatment, changing the energy of the particle beam is necessary can be compensated. The effect on the beam of charged particles is kept to a minimum by means of the beam property monitoring process in order to attain a transmission efficiency of the beam from the accelerator to the treatment location that is suitable for the treatment. The measuring and beam adjustment program to be carried out before the commissioning of the particle beam therapy system can thus be restricted, and a stable, interruption-free operation can be ensured after the treatment is started.

On the one hand, this can be attained by restricting the interaction of the beam property monitor to the halo region of the particle beam. The halo region is the external border area of the beam, seen in a cross-section in a direction perpendicular to the beam path. If the particle density distribution in the cross-section through the beam centre, i.e. the beam profile, is for instance presented by means of a Gaussian curve (other distributions are also possible), the halo region can be defined as the border area in which the density is reduced by a specific value, e.g. several orders of magnitude (such as a thousandth part), as against the maximum particle density in the central part of the beam.

In this manner, it is ensured that the particles in the central part of the beam are transported to the treatment location without being vastly affected, i.e. without major transmission losses, whereas only a comparatively low number of particles at the beam border are used for property determination with possible losses. Preferably, the spatial expansion of the beam property monitor in the direction of the beam path is kept minimal in order to keep the interaction path of the particles in the halo region with the material of the beam property monitor low.

Additionally or alternatively, it is also possible to carry out the beam property monitoring process using the electromagnetic fields generated by the beam of charged particles. In this way an influence on the beam properties in the sense of an increase of the phase space volume occupied by the beam particles by means of a direct interaction of the particles with the beam property monitor can be avoided to a large extent. Here, the phase space of the beam particularly represents the spatial expansion of the beam in two orthogonal directions perpendicular to the beam path, its divergence behavior as well as its momentum variance along these directions transverse to the beam path.

In order to enable fast correction of deviations during a treatment, the control unit is preferably designed for prompt registration and processing of the signals of the beam property monitor. If the measured data of the beam property monitor is transferred to the control unit in an analogous form, this requires an update to a digital format, in the form of calculation of digital control signals, for instance, and the transfer to the beam guiding unit and its magneto-optic elements.

Based on the measurements of beam property monitors, special computer software implemented in the control unit calculates the position and angle deviation of the centre (centroid) of the particle beam at the isocenter and the magnetic field strengths and field directions of the relevant multi-pole magnets of the beam guiding unit, which are required for correction. If a raster scan therapy method is carried out using the particle beam therapy system, the magnetic field strengths and field directions needed for adaptation of the desired actual properties regarding the centroid position and momentum can additionally be calculated, as specified by the sequence of the raster scan therapy method. The relevant adjustments are then carried out via the computer-controlled control unit with minimum time delay.

It is possible to arrange at least two beam property monitors along the beam path. In this manner, it is possible to correct a deviation in the position and angle (in other words, momentum) of the beam of charged particles in a coordinate direction transverse to the nominal beam path. It is also possible to arrange other monitors along the beam path for monitoring the beam of charged particles. These other monitors can be positioned right behind the accelerator and/or right in front of the treatment location.

The beam property monitor (and if required several beam property monitors) can record the position and/or momentum of the beam transverse to the beam path in at least one dimension. The entire transverse section of the phase space of the particles is preferably recorded by the beam property monitor or monitors. A particularly reliable beam property monitoring is thus ensured.

In a favorable arrangement, the beam property monitor can have a detection surface orthogonal to the beam path, wherein the detection surface overlaps with the beam cross-section in the halo region. Restricting the interaction of the particles with the beam property monitor to the beam periphery in the halo region keeps the degradation of the beam, in particular due to the monitoring process, to a minimum.

The control unit can be arranged such that the actual properties of the beam can be determined from the measurements of the beam property monitor taking into account calibration data. In particular, the calibration data make it possible to extrapolate to the spatial centre of the beam (which may correspond with the position of the maximum of the particle density in case of a symmetrical beam) on the basis of the measured data recorded on the periphery of the beam such as the halo region.

For this purpose, the profile of the beam in a section transverse to the beam path is preferably measured before the first commissioning—and then, if necessary, between the individual operating periods of the particle beam therapy system—and these measured data are provided to the control unit as calibration data for processing. Based on a current measurement of the beam properties on the periphery of the beam, the beam profile between the measuring points can be evaluated with high accuracy using the calibration data.

In a favorable manner, two beam property monitors are arranged diametrically opposite each other on the periphery of the beam. The beam property monitoring method can thus be carried out with high reliability since the decrease of a beam property measuring signal at one side of the periphery of the beam due to a shift in the beam position simultaneously leads to an increase of the signal from the diametrically opposite side. Moreover, the quality of the determined actual properties of the beam can be improved because the calibration data evaluation can be based on a considerable amount of measurements.

The beam property monitor can have at least one scintillation counter. In particular, several scintillation counters can also be arranged on the periphery of the particle beam as scintillation counter arrays.

The scintillation material can have a thickness of approx. 0.5 to 2 mm in the direction of the beam path. The interaction path between the particles and the beam property monitor in the halo region and thus the effect of the beam properties can thus be reduced. This also enables an especially better prevention of a beam blow up which can be detrimental to the transmission efficiency.

The beam property monitor can have at least one preferably cylindrical ionization chamber. Several ionization chambers can be arranged in several monitor sections in the direction of the beam path. Cylindrical ionization chambers have a wire-shaped electrode around which a hollow-cylindrical counter-electrode that is maintained at a different electrical potential is arranged concentrically (this type of structure is also called a straw tube structure).

The beam property monitor can additionally or alternatively quantitatively verify the electromagnetic field which is connected to the high-frequency current of charged particles in the beam.

For this purpose the beam property monitor can have at least one electrode outside the beam in which electrical charges are induceable, i.e. can be induced. This structure ensures that there is no immediate interaction between the beam property monitor and the beam particles. Instead, the beam property monitoring method is carried out via the electromagnetic fields generated by particles flowing in the beam. The risk of an influence on the beam, especially in the form of beam blow up, can thus be eliminated in most cases.

The beam property monitor can also have at least one SQUID detector. A superconducting quantum interference device (Superconducting Quantum Interference Device—

SQUID) is especially adapted for accurate measurements of minor magnetic field changes and thus enables an extremely accurate beam property monitoring without a direct interaction with the particles of the beam pulsed by the high-frequency system of the accelerator.

The beam property monitor can also be arranged outside the vacuum field of the beam guiding unit. This structure enables more liberties as regards the structure and arrangement of the beam property monitors which are not restricted by the limited space in the vacuum field.

In a favorable structure, the beam property monitor is movable transversely to the beam path. This makes it possible to react more flexibly to deviations in the beam properties, especially in the beam centroid position, and the influence on the particle beam is thus kept low by the beam property monitoring method.

In particular, the mobile structure ensures that the beam property monitor tracks the halo region of the beam which may be shifted in accordance with the raster scan regulation of a raster scan therapy method, if necessary. Moreover, the mobility of the beam property monitors also makes it easier to determine the calibration data.

Another favorable structure could be wherein the beam guiding unit has scan magnets for raster scanning, wherein the control unit is set up such that the first control signals are generated for carrying out a raster scan therapy method and second control signals are generated on the basis of the determined deviations for adaptation of the beam properties, and such that third control signals are generated from the first and the second control signals and are transmitted to the scan magnets. In this manner, scan magnets which act as magneto-optic elements and ensure a shift of the beam of charged particles as prescribed in the raster scan therapy method, can thus also be used along the beam path, preferably in a beam path section located in the gantry, for the correction of unforeseeable position and momentum deviations that occur, for instance, when rotating the gantry or changing the energizing current in the magnetic field coils. The device-related costs for the implementation of the particle beam therapy system can thus be reduced.

Alternatively the beam guiding unit can also include scan magnets for raster scanning and correction magnets, especially made of laminated iron, wherein the control unit is set up such that the first control signals are generated for carrying out a raster scan therapy method and the second control signals are generated on the basis of the determined deviations from the nominal beam properties, and such that the first control signals are transmitted to the scan magnets and the second control signals are transmitted to the correction magnets.

The scan magnets, with correction function if required, and/or the correction magnets can adapt the actual properties of the particle beam in four dimensions of the transverse phase space (two spatial dimensions transverse to the beam path and the momentum dimensions conjugated to them) to the desired properties. To enable a fast correction, laminated iron is particularly appropriate. Thus the influence of eddy-currents can be kept minimal and the magnetic fields required for guiding and correcting the beam can be set to the required values within fractions of a second.

It is also possible to position scan magnets in the particle beam therapy system which are used for carrying out the raster scan therapy method as well as for correcting beam deviations, and to also use special correction magnets at other points along the beam path which are used only for correcting deviations.

The beam guiding unit can have a gantry, in particular a rotable gantry, before at least one treatment location. In a particular structure, several treatment rooms can be used instead of just one, which have individually designed gantries that deviate from each other, wherein the beam of charged particles is guided in the relevant treatment room on the basis of its properties such as particle energy or angular divergence using a magneto-optic unit at the gantry that is adapted to these properties.

The gantry can preferably be rotated by up to 360°, in particular around a horizontal axis, in order to irradiate the treatment location from maximum possible angles. The gantry also preferably comprises a magneto-optic unit mounted on it which has beam deflection and/or beam formation elements such as multi-pole magnets (di-pole magnets, quadru-pole magnets, sextupole magnets, etc.) for beam guiding and beam formation in order to switch, deflect, focus and/or collimate the particle beam from a prior direction to the treatment location.

The gantry also preferably includes at least one additional beam property monitor. This helps in determining the actual properties close at the treatment location and enables correction with increased accuracy.

The beam guiding unit can have several magneto-optic units, especially in the form of multi-pole magnets.

Preferably a magneto-optic collimator is subordinated to the beam property monitor in the beam path. A magneto-optic collimator can be used to select a section of the phase space volume presented by the beam particles for forwarding to the treatment location.

According to another theory, the object of this invention is to provide a method for guiding a beam of charged particles in a particle beam therapy system which comprises the following steps: Generating a beam of charged particles; guiding the beam of charged particles to a treatment location via a beam guiding unit; recording the beam properties with at least one beam property monitor arranged along the beam path, wherein at least one beam property monitor is arranged on the beam periphery that is perpendicular to the beam path such that the beam properties are recorded by means of direct interaction with the beam particles in the halo region and/or indirectly by means of electromagnetic interaction; determining the deviations of the actual properties from the desired properties of the beam via a control unit that communicates with the beam property monitor or monitors; determining control signals on the basis of the deviations for adaptation of the beam properties; transmitting the control signals to the beam guiding unit that communicates with the control unit.

The control unit can determine the actual properties of the beam from the measurements of the beam property monitor taking into account the calibration data.

The control unit can also generate first control signals for carrying out the raster scan therapy method and second signals on the basis of the determined deviations for adaptation of the beam properties, wherein third control signals are generated from the first and the second control signals and transmitted to scan magnets which are arranged at the beam guiding unit for raster scanning.

The control unit can alternatively generate first control signals for carrying out the raster scan therapy method and second signals on the basis of the determined deviations for adaptation of the beam properties, wherein the first control signals are sent to scan magnets which are arranged at the beam guiding unit for raster scanning and the second control signals are sent to correction magnets, especially those made of laminated iron, which are arranged at the beam guiding unit.

With respect to further advantages or advantageous designs the explanations concerning particle therapy systems in accordance with this invention are referred to.

Particle beam therapy systems with designs in accordance with this invention would be advantageous.

Using a particle beam therapy system as described above for irradiation of tissues, especially human tissues, is preferred.

Using a particle beam therapy system as described above for tumor therapy, especially in humans, is preferred.

There are various methods for designing and developing particle beam therapy systems or methods that are in accordance with this invention. For this, the dependent patent claims on the one hand and the description of embodiments along with the enclosed drawings on the other are referred to.

DETAILED DESCRIPTION OF THE INVENTION

Figure 1:
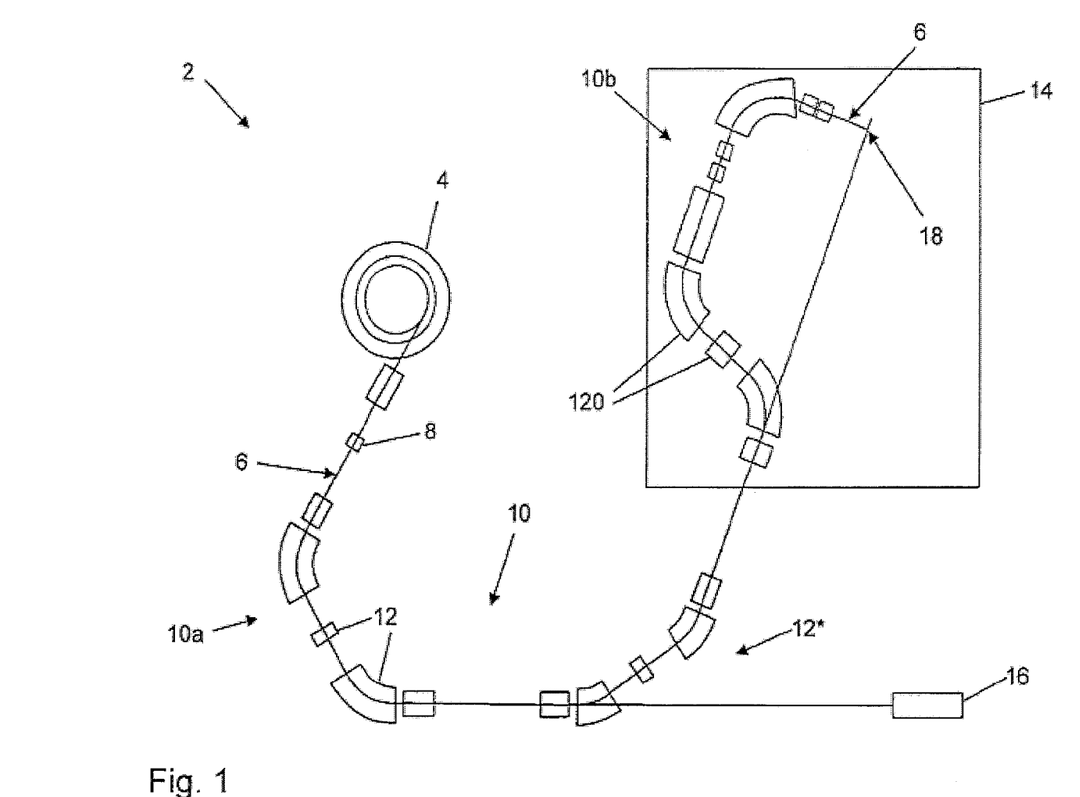
FIG. 1 A schematic overview of a particle beam therapy system.

FIG. 1 shows an embodiment of a particle beam therapy system 2 as per this invention as a schematic overview. The particle beam therapy system 2 includes an accelerator 4 in the form of an especially superconducting cyclotron which can accelerate the charged particles up to an energy of 200 to 250 MeV and provide them in pulses with a frequency of, for instance, 72 MHz. If maximum energy is not required, the beam path 6 has energy correction unit 8 in the form of a degrader for the correction of energy of the particle beam. After passing through the degrader 8, the beam path 6 of the particle beam passes through the beam guiding unit 10. The beam guiding unit 10, in this example, comprises a beam transfer unit 10a with several magneto-optic elements 12 which guide the particle beam from accelerator 4 to treatment room 14.

The particle beam is deflected towards the treatment room 14 using a magneto-optic deflector 12*, in the form of a system of di-pole and quadruple magnets for instance. A beam collection unit 16 is located in the beam direction behind the magneto-optic deflector 12* for reasons of safety.

Magneto-optic elements 120 which are assigned to the beam guiding unit 10 as 10b are arranged in the treatment room 14 in the form of beam deflection elements and beam formation elements (e.g. for collimation or focusing). The magneto-optic elements 120 ensure that the particle beam is supplied to treatment location 18 as per the prescribed conditions, such as the focusing degree and/or high transmission efficiency. The relevant section 10b of beam guiding unit 10 is arranged in treatment room 14 preferably on a rotatable gantry (not shown) enabling the magneto-optic elements 120 controlling the beam path 6 to be rotated (up to 360°) around the treatment location 18 in order to be able to set different irradiation angles.

Figure 2A:
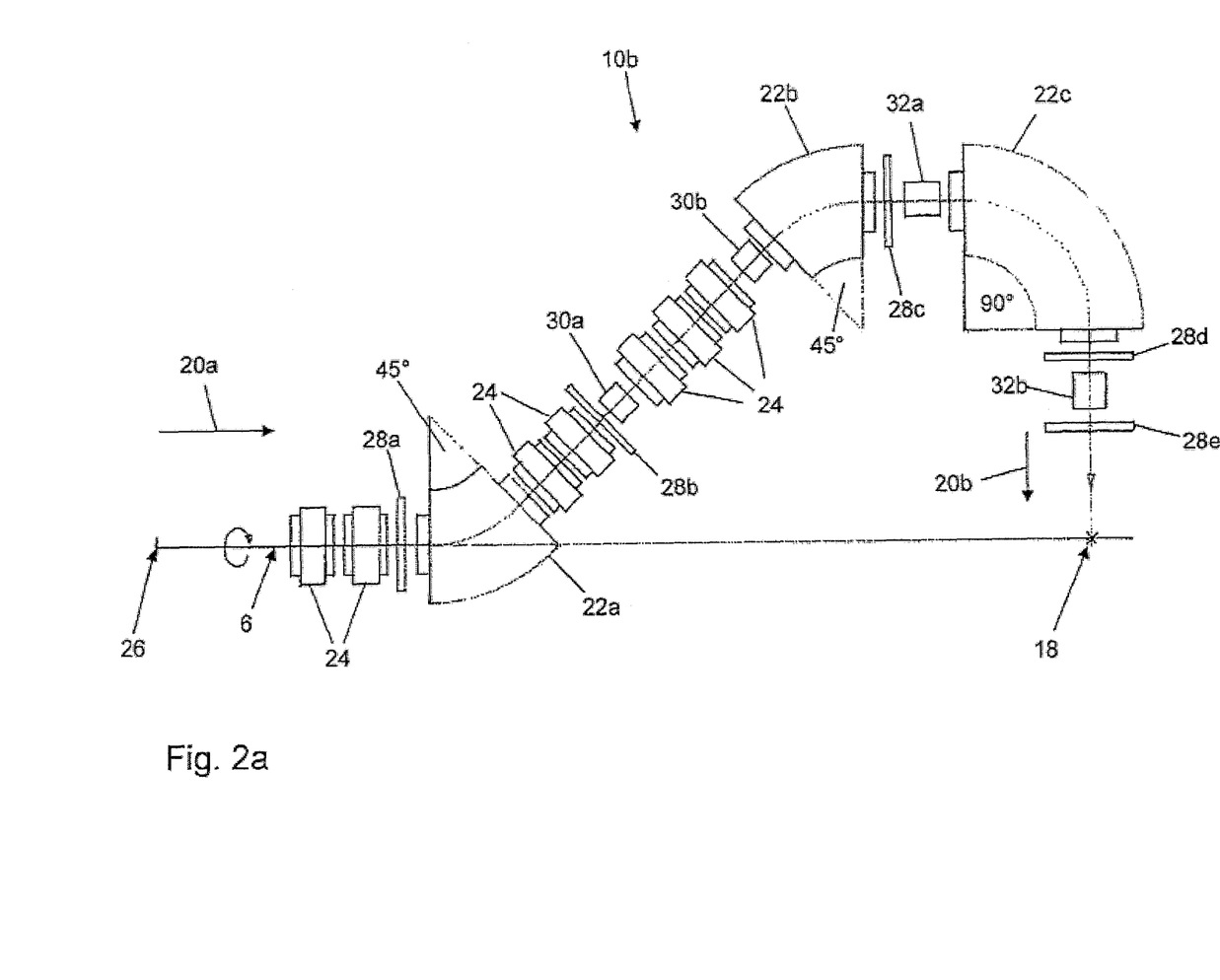
FIG. 2a-b The structure of the beam guiding unit at a gantry.

An example of a possible structure of the beam guiding unit 10b at a gantry has been presented in FIG. 2a. From the beam incidence direction 20a set via the magneto-optic deflector 12*(FIG. 1), the particle beam is deflected thrice in the further course of the beam path in order to then adopt direction 20b which is perpendicular to the original beam incidence direction 20a. The intersection point of the extended beam incidence direction 20a with the beam that has been deflected thrice is called the isocenter and marks the treatment location 18, i.e. the location where a target is exposed to the particle beam.

DETAILED DESCRIPTION

As the transport system of the particle beam, the beam guiding unit 10b can weigh up to several hundred tons and is thus appropriately mounted on a highly stable carrier frame ("gantry"—not shown) which, in this example, can be moved by up to 360° around the beam incidence direction 20a as the rotary axis.

The magneto-optic elements assigned to the beam guiding unit 10b on the gantry, in this example three deflection magnets 22a, 22b and 22c and several quadruple magnets 24 are used to ensure the transport of maximum phase space volume of charged particles from the entry point 26 to the isocenter 18 where the beam hits the rotational axis at an angle of about 90°. In order to ensure the required rotation symmetry, the particle beam preferably shows rotational symmetry at the entry point 26 of the gantry in the room coordinate section transverse to beam path 6 and a momentum dispersion of almost zero. In this manner, a small beam cross-section of just a few square millimeters can be attained at isocenter 18 for application of a raster scan therapy method.

The particle beam propagates in the gantry along the rotation axis of the gantry passing through entry point 26 and isocenter 18. It then enters the first two quadruple magnets 24 wherein there is refocusing. It then passes through the first beam position monitor 28a which, in this example can be constructed as a straw tube arrangement, and then through a di-pole magnet acting as a deflection magnet 22a, which deflects the particle beam by 45°.

After passing through two more quadruple magnets 24, the beam passes through another beam position monitor 28b in the form of a straw tube arrangement and is, if needed, corrected in the correction magnets 30a subordinated to it with reference to a position transverse to beam path 6 (preferably the relevant momentum coordinate as well). After passing through the quadruple magnets 24, the beam passes through a second correction magnet 30b where it is corrected with reference to the transverse position that is orthogonal to the previously mentioned transverse direction (and preferably the relevant momentum coordinate as well). It then passes through another 45° deflection magnet 22b due to which it once again propagates parallel to the rotation axis of the gantry. It then passes through another beam position monitor 28c in the form of a straw tube arrangement and then the first scan magnet 32a for raster scanning, by which the beam is scanned over the requested space and momentum. The beam is then finally deflected by 90° through another deflection magnet 22c in the direction of the target at the isocenter 18 (e.g. the tumor tissue) and scanned using a further scan magnet 32b thus enabling the complete raster scan over the requested space and momentum. This is controlled via two more beam position monitors 28d and 28e, for instance, in the form of straw tube arrangements, subordinated and superordinated to the second scan magnet 32b in the beam path 6.

Figure 2B:
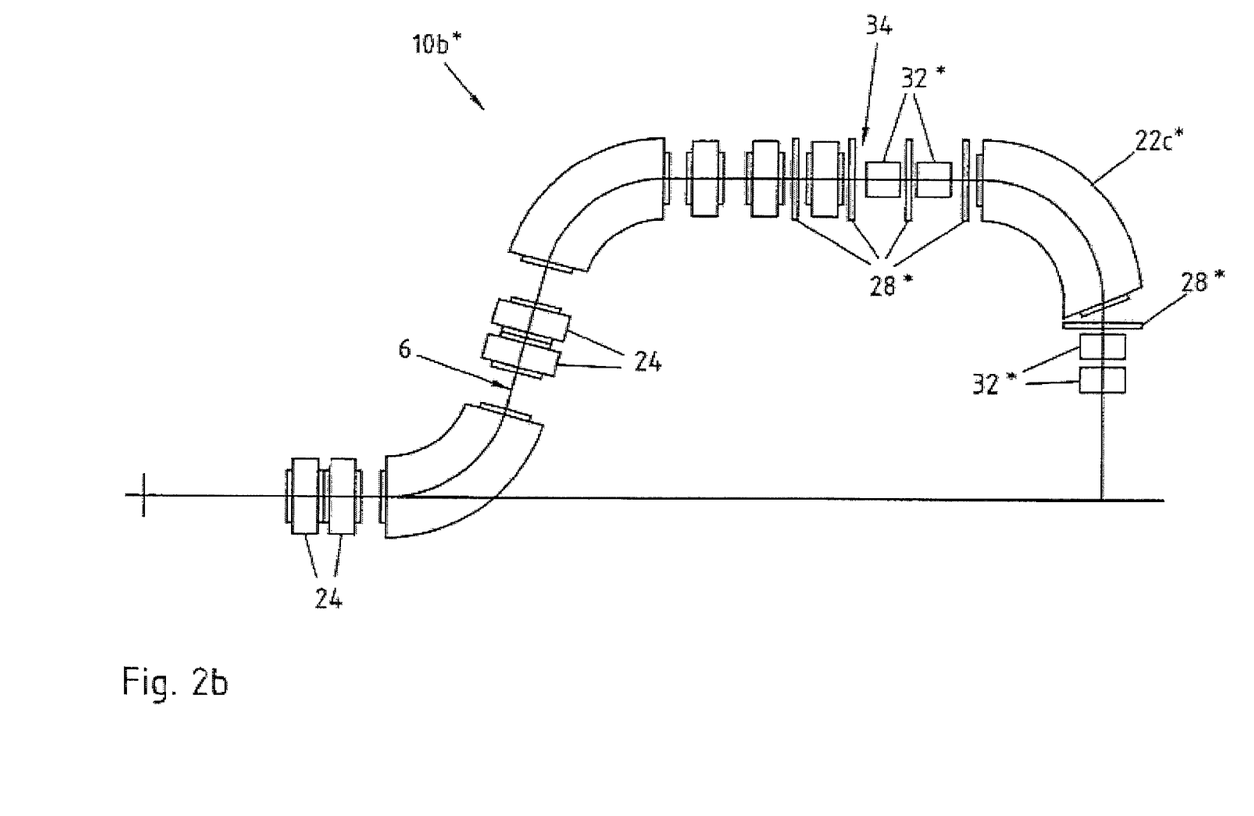

FIG. 2b shows a similar structure of the beam guiding unit 10b* on a gantry.

Functionally comparable elements have been included with the same reference markings as in FIG. 2a. Only the differences from the beam guiding unit 10b in FIG. 2a have been explained below. In contrast to FIG. 2a, the beam guiding unit 10b* has four scan magnets 32* each of which can be used for raster scanning of the particle beam in a dimension transverse to beam path 6. The spatial alignment of the particle beam can thus be specifically changed as per the specifications of the raster scan therapy method using scan magnets 32*. In addition to carrying out the raster scan therapy method, the scan magnets 32* can also correct the unforeseeable deviations. The arrangement of additional correction magnets (see 30a, 30b in FIG. 2a) that have been specially designed for correction of deviations is thus no longer required. The device-related cost of the particle beam therapy system can thus be reduced. A collimator (not shown) can be subordinated to the relevant beam property monitor 28* at the point marked with 34 in the beam path 6. The width of the beam profile can be reduced using this variant of the beam guiding unit 10b*. The design of the beam-guiding magneto-optic elements, especially the 90° deflection magnets 22c*, in the beam path 6 can thus be simplified. This simplified design of the magneto-optic elements leads to favorable cost savings. This variant is especially suitable if both the beam position monitors 28* superordinated to point 34 in the beam path 6 are sufficient for correcting the beam property deviations.

The measured data of the five beam position monitors 28* in this example are used by a control unit (not shown) taking into account the calibration data to determine the deviations of the actual properties of the beam from its desired properties (i.e. nominal properties) and to generate control signals for correction on the basis of these deviations. These second control signals for correction along with the first control signals for carrying out a raster scanning therapy method can be processed, e.g. in a way of superimposing, into third control signals.

A fast electronic control unit implemented in the control unit is used for the registration and processing of signals (if required analogue signals) of at least two beam position monitors 28, 28*(as shown in FIGS. 2a and 2b) and their digital formats. Here, the signals of the beam position monitors 28, 28* located on the periphery of the beam, and, where appropriate, those of monitors located further in the beam path 6 can be used for calculating the position and momentum deviation of the beam and thereby for calculating the control signals for the correction magnets which are required for the correction of the beam (see 30a, 30b in FIG. 2a). This enables an automatically controlled correction of the particle beam along the entire beam path 6, especially in the area of the gantry.

Figure 3A:
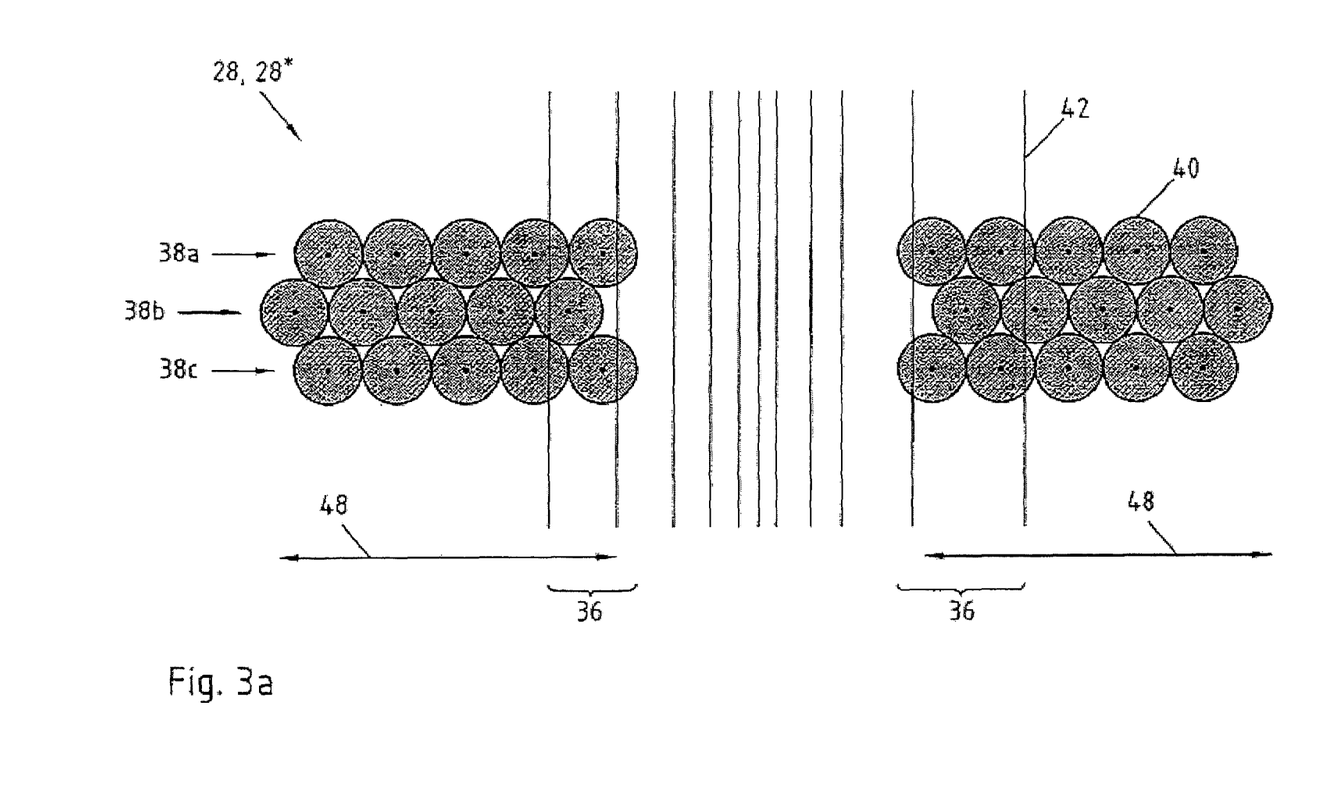
FIG. 3a-c Several exemplary embodiments for beam property monitors constructed as beam position monitors, and FIG. 4 Results of a Monte-Carlo simulation for determining the accuracy of the measurement of the displacement.

FIG. 3a shows the principle of a beam position monitor 28, 28a which has a detection surface orthogonal to the beam path 6, whereby the detection surface in the halo region 36 overlaps with the beam cross-section which extends into the halo region 36 of the particle beam at least partly.

In this example, the beam position monitor 28, 28* shows three sections 38a, 38b and 38c of cylindrical ionization chambers 40—straw tubes—one after the other in the direction of the beam path, whereby three sections 38a, 38b and 38c are mounted on the opposite sides of the beam diametric to each other. Two or more sections of cylindrical ionization chambers 40 can also be present. The cylindrical ionization chambers 40 can be operated in the vacuum of the beam guiding unit 10b*. They are movable (e.g. independently) using a control unit (not shown) from both sides in the direction of the desired position of the beam centre marked here with the help of the beam lines 42 located nearer to each other.

Figure 3B:
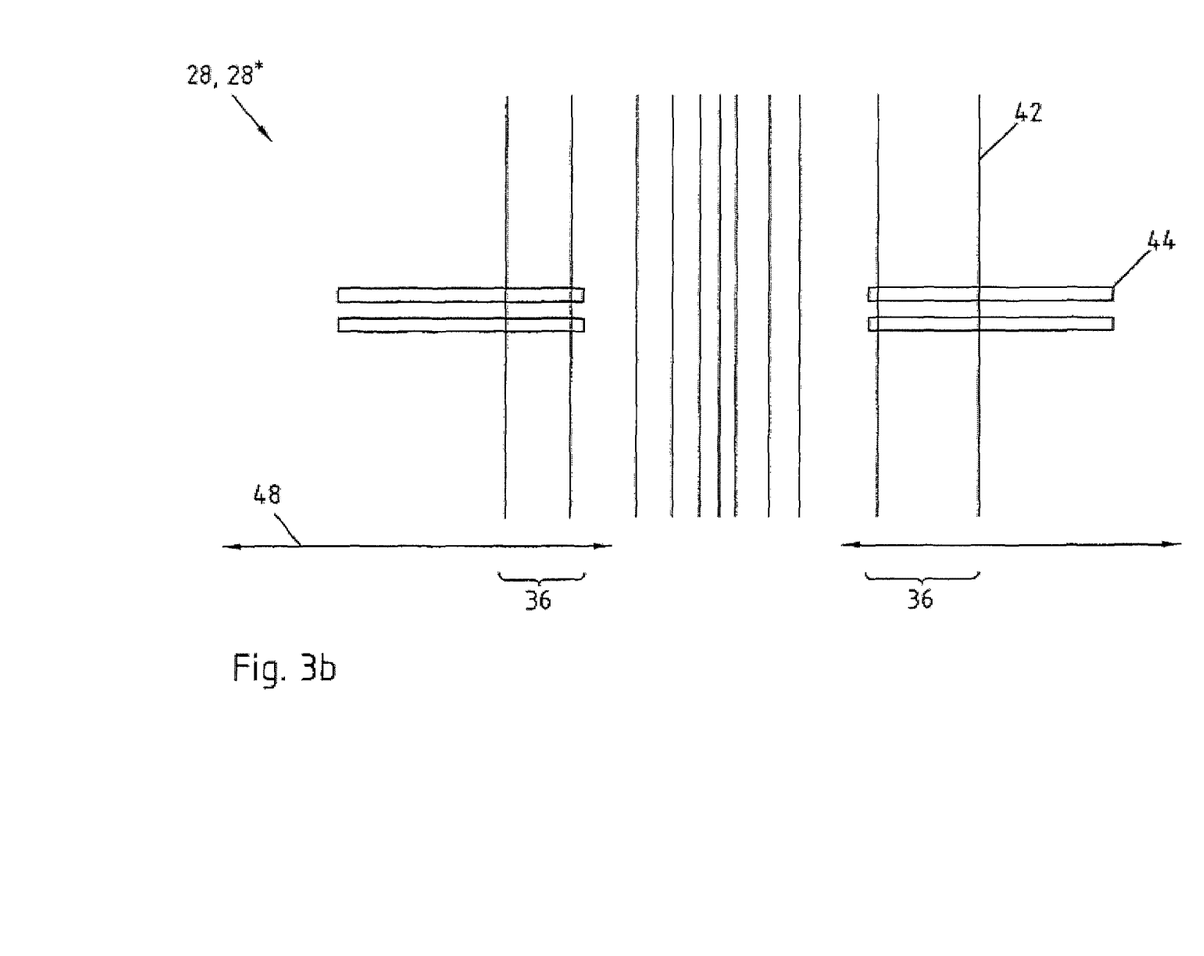

FIG. 3b shows the principle of another beam position monitor 28, 28* which has two thin scintillation counters 44 on two sides of the particle beam diametric to each other. These scintillation counters 44 can also be operated in vacuum. The scintillation counters 44 arranged on one side along the beam path 6 should be preferably connected in coincidence. The light generated in the scintillation material by a particle from the halo region 36 of the beam passing through the counter is led to the photo cathode of a photo multiplier (not shown) via a light conductor (where appropriate with a wavelength shifter). The coincidence circuit of the current pulse of the photo multiplier helps in ensuring that only the signals of the pass-through charged particles are registered on each side of the beam. The preferred extension of the scintillation material in the direction of the beam path is between 0.5 and 2 mm.

The transverse profile of the beam of charged particles need not be necessarily symmetrical as indicated by the density of lines 42.

Figure 3C:
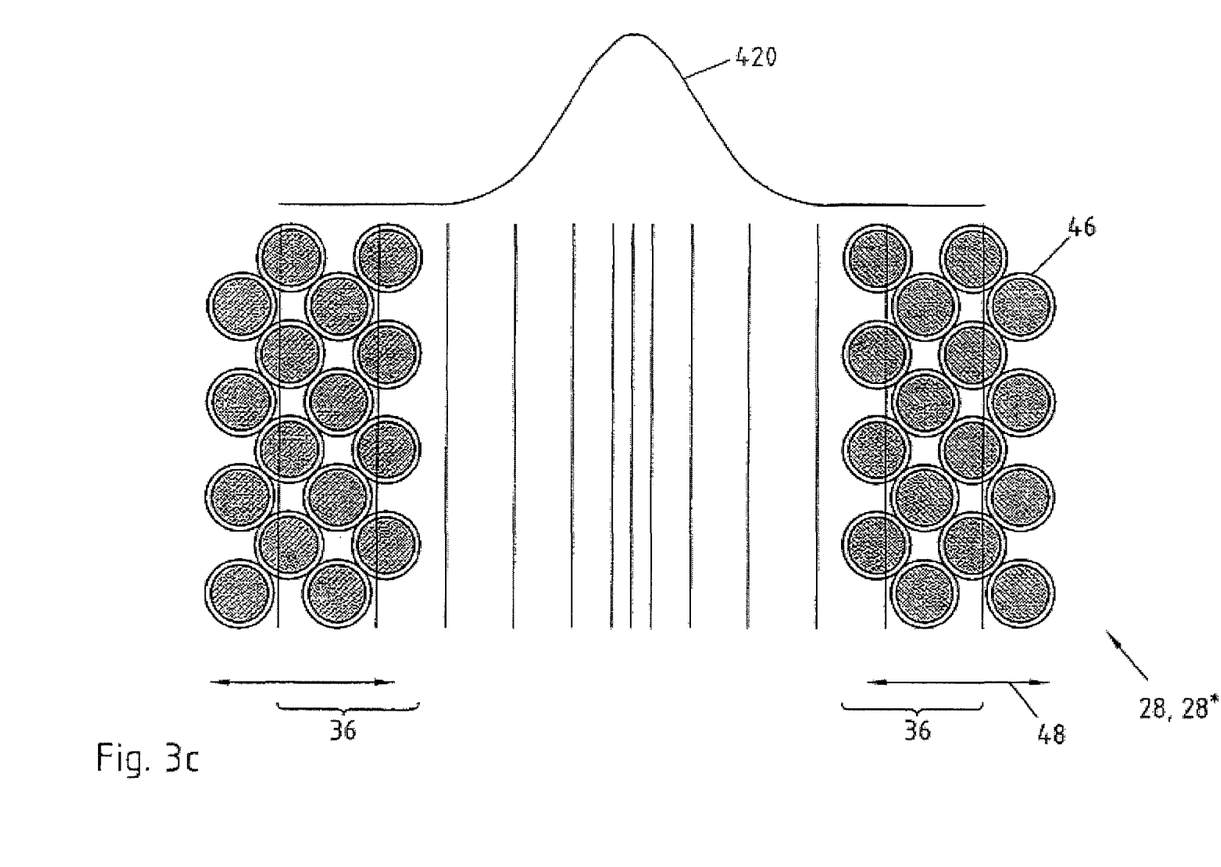

FIG. 3c shows the principle of another beam position monitor 28, 28* which shows several layers of organic or inorganic scintillating fibers 46. Even these fibers 46 are suitable for vacuum. The recorded signals are read out either directly or via an intermediately connected light conductor and multi-channel photo multiplier (not shown). A possible transverse distribution of the beam of charged particles marked with the beam lines 42 has been shown in FIG. 3c in the form of a normal distribution 420.

Organic scintillation material is irradiation hard only to a limited extent. In order to increase the life of beam position monitors 28, 28* containing organic scintillator material, the scintillation counter can be shifted after a specific operating period such that an area of scintillator material that has been used so far for recording the beam properties is moved out of the halo region 36 and a field that has not been used so far for the recording can be moved into it.

As can be seen from the double-headed arrows 48 in the FIGS. 3a to 3c, the beam position monitors 28, 28* can be moved from the beam periphery in the direction of the desired position of the beam centre symmetrically or asymmetrically.

Beam position monitors (not shown) which are arranged on the beam periphery outside the beam and record the beam properties on the basis of the electromagnetic fields generated on the basis of the flowing beam particles can also be used in addition or as an alternative to the beam position monitors 28, 28* which have a direct interaction with the beam particles in the halo region 36. The beam position monitor 28, 28* can for instance have at least one electrode (not shown) arranged outside the beam in which electrical charges are induceable. The beam position monitor 28, 28* can additionally or alternatively have at least one SQUID detector (not shown).

Figure 4:
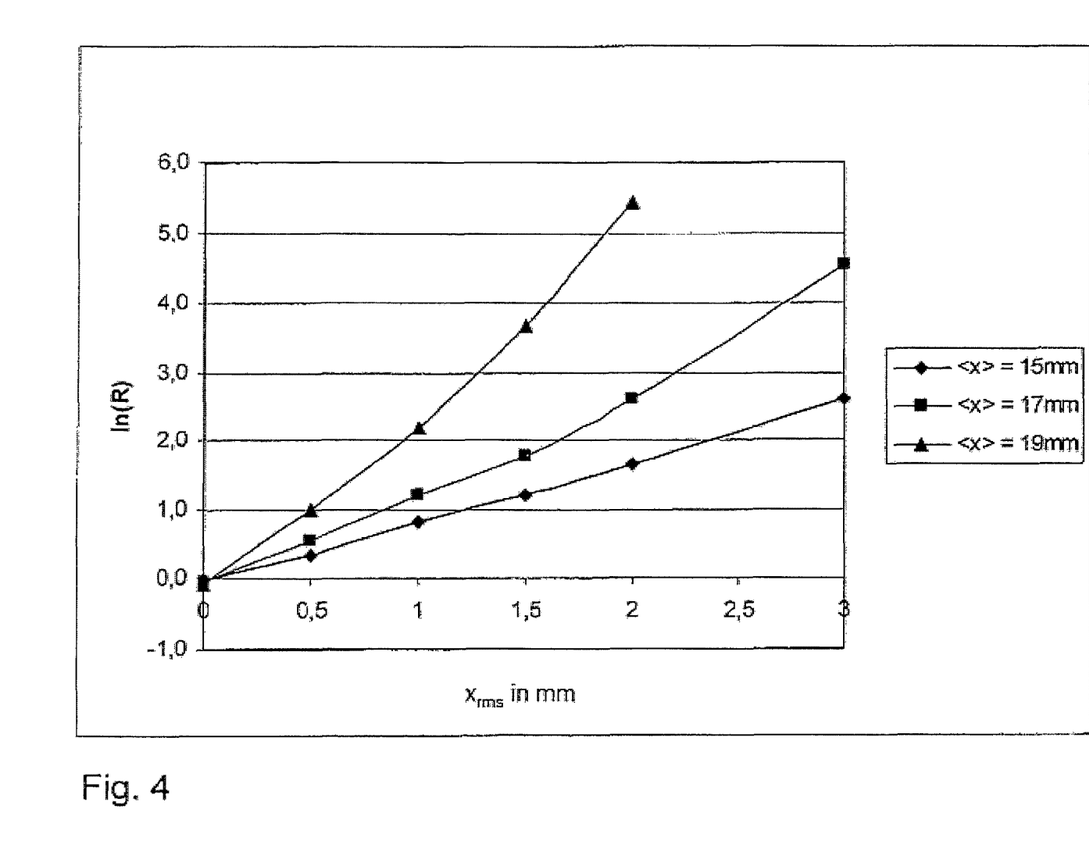

FIG. 4 gives an example for the accuracy with which a position deviation of the beam centre from the desired position can be determined. In this example, it is assumed that the beam position monitor 28, 28* is located directly in front of the scan magnets in the gantry (see FIG. 2b).

The particle counting rates N1 and N2 in two diametrically opposite fields in the region of the halo of the beam are recorded. Also a two dimensional space coordinate system is constructed which extends into a section perpendicular to the beam path 6. Both transverse axes are orthogonal to each other. Here, the zero point of the coordinate axes denotes the nominal centre of the beam (i.e. the position with the maximum number of particles or the maximum power density) if the beam is in the desired position.

The counting rate in the region of positive transverse coordinates along an axis is assigned to variable N1 (i.e. counting rate from the first beam position monitor 28, 28*) and the counting rate in the region of negative coordinates along the same axis is assigned to variable N2 (i.e. rate from the second beam position monitor 28, 28* that is diametrically opposite to the first beam position monitor 28, 28*).

Shown is the quantity ln (R)=ln (N1/N2) as function of the deviation $X_{rms}$ (rms: root mean square, average square deviation) of the actual position from the desired position in units of millimeters at the position of the beam position monitors 28, 28* along the beam path 6. The pre-requisite here is that the beam position monitors 28, 28* should be arranged symmetric to the desired position, i.e. the zero point. It is also assumed that N1 is greater than or at least equal to N2, i.e. the beam has moved from its desired position in the direction of the beam position monitor 28, 28* to which the counting rate N1 is assigned. The variable <x> to the right in FIG. 4 indicates the average distance of both beam position monitors 28, 28* from the zero point. The curves are determined on the basis of detailed Monte-Carlo simulations.

The error in measuring the logarithmic ratio of the counting rates is considerably less than one percent and the resulting accuracy of determination of $X_{rms}$ is in the range of a few tenths of a millimeter. This is sufficient to carry out a practical deviation correction.

The physical basics of interaction of protons, with the material and the programs used for calculating the properties of beam guiding systems have been described in the academic reports specified below:

Particle Data Group, W.-M. Yao et al., "The Review of Particle Physics", Journal of Physics G33 (2006)1 and update 2008.

Karl L. Brown, Sam K. Howry, "TRANSPORT, A Computer Program for Designing Charged Particle Beam Transport Systems", SLAC Report No. 91 (1970) and later updates of the TRANSPORT program by U. Rohrer and others.

U. Rohrer, "PSI Graphic TURTLE Framework based on a CERN-SLAC-FERMILAB version by K. L. Brown et al.", http://people.web.psi.ch/rohrer-u/turtle.htm (2008).

J. Drees, "Passage of Protons through Thick Degraders", Cryoelectrica Report September 2008.

The invention claimed is:

1. A particle beam therapy system comprising:
an accelerator configured to provide a beam of charged particles,
a beam guiding unit configured to feed the beam from the accelerator to a treatment location, whereby the beam guiding unit comprises a rotatable gantry with at least two beam position monitors arranged upstream of the treatment location along a beam path in the gantry and configured to detect at least one of a transverse beam position and a momentum transverse to the beam path, and
a control unit configured to communicate with the at least two beam position monitors and the beam guiding unit, to determine deviations of an actual position of the beam from its desired position and to transmit control signals to the beam guiding unit for the adaptation of the beam position based on the deviations,
wherein the at least two beam position monitors are arranged on either side of a beam periphery diametric to each other such that the at least one of the transverse beam position and the momentum transverse to the beam path are detected by means of direct interaction with beam particles in a halo region in at least one dimension, and wherein the beam position monitors each include at least two beam position monitoring elements arranged along the side of the beam path such that at least two beam position monitoring elements are arranged on each side of the beam path, each of the beam position monitors registering signals of charged particles that pass through each of the at least two beam position monitoring elements included in that beam position monitor.

2. The particle beam therapy system of claim 1, wherein at least one of the at least two beam position monitors has a detection surface orthogonal to the beam path that overlaps in the halo region with the beam cross-section.

3. The particle beam therapy system of claim 1, wherein the control unit is set up such that the actual position of the beam is determinable from the measurements of at least one of the at least two beam position monitors taking into account calibration data.

4. The particle beam therapy system of claim 1, wherein at least one of the at least two beam position monitors has at least one scintillation counter.

5. The particle beam therapy system of claim 4, wherein scintillation material of the at least one scintillation counter has a thickness of approx. 0.5 to 2 mm in the direction of the beam path.

6. The particle beam therapy system of claim 1, wherein at least one of the at least two beam position monitors has at least one ionization chamber.

7. The particle beam therapy system of claim 6, wherein the at least one ionization chamber is cylindrical.

8. The particle beam therapy system of claim 1, wherein at least one of the at least two beam position monitors is moveable transversely to the beam path.

9. The particle beam therapy system of claim 1, wherein the beam guiding unit has scan and correction magnets for raster scanning, whereby the control unit is set up such that first control signals are generated for carrying out a raster scan therapy method and that second control signals are generated on the basis of the determined deviations for adapting the beam position, and that third control signals are generated resulting from the first and the second control signals and transmitted to the scan and correction magnets in order to perform a corrected raster scan therapy method.

10. The particle beam therapy system of claim 1, wherein the beam guiding unit has scan magnets for raster scanning and correction magnets, whereby the control unit is set up such that first control signals are generated for carrying out a raster scan therapy method and second control signals are generated on the basis of the determined deviations for adapting the beam position, and that the first control signals are transmitted to the scan magnets and the second control signals are transmitted to the corrections magnets.

11. The particle beam therapy system of claim 10, wherein the correction magnets are made of laminated iron.

12. The particle beam therapy system of claim 1, wherein a magneto-optic collimator is upstream of at least one of the at least two beam position monitors in the beam path, the magneto-optic collimator directly interacting with the charged particles in the halo region of the beam.

13. A method for guiding a beam of charged particles in a particle beam therapy system, comprising:
providing a beam of charged particles;
guiding the beam of charged particles to a treatment location via a beam guiding unit;
detecting at least one of a transverse beam position and a momentum transverse to the beam path with at least two beam position monitors, wherein the at least two beam position monitors are comprised in a rotatable gantry of the beam guiding unit and are arranged upstream of the treatment location along a beam path in the gantry and on either side of a beam periphery diametric to each other such that the at least one of the transverse beam position and the momentum transverse to the beam path are detectable by means of direct interaction with beam particles in a halo region in at least one dimension, the beam position monitors each including at least two beam position monitoring elements arranged along the side of the beam path such that at least two beam position monitoring elements are arranged on each side of the beam path;

registering only signals corresponding to charged particles that pass through the at least two beam position monitoring elements;

determining deviations of an actual position of the beam from its desired position based on registered signals via a control unit configured to communicate with the at least two beam position monitors;

determining control signals on the basis of the deviations for adapting the beam position; and transmitting the control signals to the beam guiding unit configured to communicate with the control unit.

14. The method of claim 13, wherein the control unit is configured to determine actual properties of the beam from measurements of at least one of the at least two beam position monitors taking into account calibration data.

15. The method of claim 13, wherein the control unit is configured to generate first control signals for carrying out a raster scan therapy method, second control signals on the basis of the determined deviations for adaptation of the beam properties and third control signals resulting from the first and the second control signals, and to transmit the third control signals to scan magnets arranged at the beam guiding unit for raster scanning.

16. The method of claim 13, wherein the control unit is configured to generate first control signals for carrying out a raster scan therapy method and second control signals on the basis of the determined deviations for adaptation of the beam properties, to send the first control signals to scan magnets arranged at the beam guiding unit for raster scanning and to send the second control signals to correction magnets arranged at the beam guiding unit.

17. The particle beam therapy system of claim 1, wherein the accelerator is a cyclotron.

* * * * *